(12) United States Patent
Hopkins et al.

(10) Patent No.: US 11,304,986 B2
(45) Date of Patent: Apr. 19, 2022

(54) METHODS OF EXTRACTION OF PLANT MATERIALS AND EXTRACTS OBTAINED USING SUPERCRITICAL GLYCERIN

(71) Applicants: Demitri J Hopkins, West Sacramento, CA (US); Michael Willems, West Sacramento, CA (US)

(72) Inventors: Demitri J Hopkins, West Sacramento, CA (US); Michael Willems, West Sacramento, CA (US)

( * ) Notice: Subject to any disclaimer, the term of this patent is extended or adjusted under 35 U.S.C. 154(b) by 0 days.

(21) Appl. No.: 16/904,072

(22) Filed: Jun. 17, 2020

(65) Prior Publication Data
US 2021/0393718 A1    Dec. 23, 2021

(51) Int. Cl.
*A61K 36/00* (2006.01)
*A61K 36/185* (2006.01)
*B01D 11/02* (2006.01)
*A61K 31/05* (2006.01)
*A61K 31/352* (2006.01)

(52) U.S. Cl.
CPC ............ *A61K 36/185* (2013.01); *A61K 31/05* (2013.01); *A61K 31/352* (2013.01); *B01D 11/0203* (2013.01); *B01D 11/0288* (2013.01); *A61K 2236/37* (2013.01)

(58) Field of Classification Search
CPC ...................................................... A61K 36/00
USPC .......................................................... 424/725
See application file for complete search history.

(56) References Cited

U.S. PATENT DOCUMENTS

2010/0196488 A1* 8/2010 Whittle ..................... A61P 1/00
424/489

FOREIGN PATENT DOCUMENTS

BR          201216970      * 2/2016

* cited by examiner

*Primary Examiner* — Michael V Meller
(74) *Attorney, Agent, or Firm* — Saralynn Mandel

(57) ABSTRACT

A method for extracting bioactive compounds from plant materials using supercritical glycerin and at least one inert co-solvent that lowers the effective supercritical point of the supercritical glycerin to its boiling point, and the extracts obtained from the method.

4 Claims, 1 Drawing Sheet

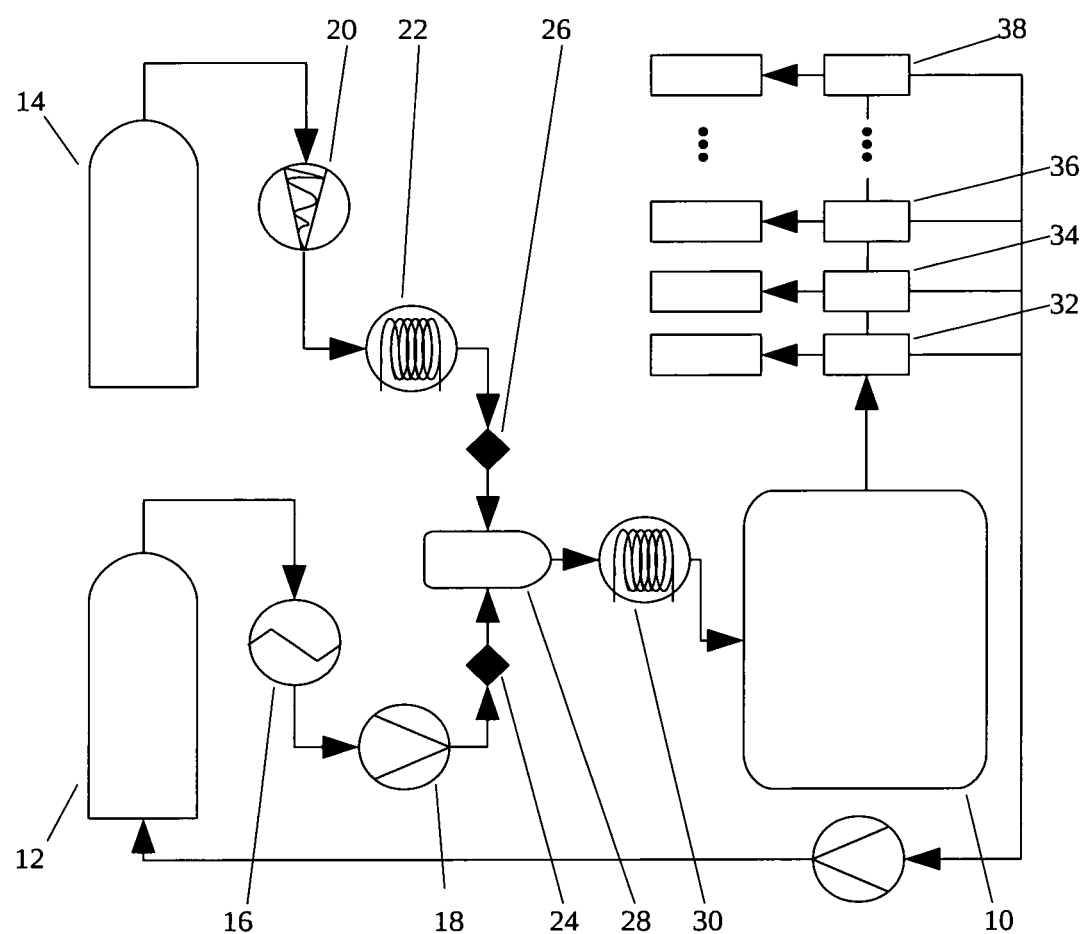

METHODS OF EXTRACTION OF PLANT MATERIALS AND EXTRACTS OBTAINED USING SUPERCRITICAL GLYCERIN

FIELD OF THE INVENTION

The present invention relates to methods of extraction of plant materials using supercritical glycerin, and in particular to methods of extraction used to obtain bioactive compounds from plant materials.

BACKGROUND OF THE INVENTION

Extraction of plant materials is now used to obtain bioactive compounds which may be used as supplements and/or treatments for a variety of conditions, and generally to improve the well-being of human, animal and plant life. For example, extraction of cannabinoids such as THC and CBD and other bioactive compounds from Cannabis has become the basis for a number of commercial products, including therapeutics, which are provided in many forms including as "oil" for use in vaporizing devices.

Traditional methods for the extraction of bioactive compounds from plant materials, such as maceration and distillation have a number of disadvantages including long extraction times, a requirement for large amounts of toxic solvents, low efficiency, and environmental pollution. Moreover, these processes can cause degradation of thermolabile compounds present in the plant material. Supercritical fluid extraction (SFE) is the process of separating one component (the extractant) from another (the matrix) such as plant materials, using supercritical fluids as the extracting solvent with or without additional solvents ("co-solvents"). The liquid-vapor boundary terminates in an endpoint at a critical temperature and critical pressure known as the "critical point." Extraction may be performed using a solid or liquid matrix and is done above the critical temperature and critical pressure points of the supercritical fluid, where distinct liquid and gas phases do not exist. SFE can be used to remove unwanted material from a product (e.g. decaffeination of coffee or tea) or to collect desired products, such as bioactive compounds from plant material.

SFE is a green technology that offers several advantages over conventional extraction methods using solvents, providing higher selectivity and shorter extraction times. Supercritical fluids (SCFs) have higher diffusivity and lower density, viscosity, and surface tension than traditional solvents. SFE methods of plant materials are known, using supercritical $CO_2$. (Wrona et al., J. of AOAC International, (2017) 100(6):16-24-1635, and Sexton et al., Planta Med (2018) 84(4):234-241). Recently, improved methods for SFE using ultra-high-performance supercritical fluid chromatography and diode/array mass spectrometric detection have been developed. (Wang et al., J. Forensic Sci. (2017) 62(3):602-611).

Carbon dioxide ($CO_2$) is the most commonly used solvent in SFE sometimes modified by co-solvents such as ethanol or methanol. The qualitative and quantitative composition of the final extract in SFE is determined by the physicochemical properties of the solvent and parameters of the process that include temperature and pressure, as well as characteristics of the sample plant material.

Disadvantages of SFE using $CO_2$ include: an end product extract with relatively high viscosity and requirement for additional processing requirements to obtain an optimal extraction product. The product made by supercritical extraction of cannabis, known as "oil," is used in vaporizers such as "pens" for consumption, but the viscosity of SFE with $CO_2$ makes it prohibitively difficult to mix into vaporization fluids like glycerin and propylene glycol. This has resulted in the current version of vaporizers with pure cannabis extract oil and a disposable glass cartridge holding the oil. This vaporizer technology generates waste, is inconvenient, and fails due to cartridge breakage. Further generations of vaporizers require the active ingredient be suspended in a solution of glycerin. This is done at present for some cannabis extractions, but ends up being time-consuming and costly, and thus non-competitive.

Glycerin (also known as "Glycerol") has been used as "green solvent" in organic synthesis reactions. The supercritical point temperature of glycerin is 850° Kelvin (577° C.) and the supercritical pressure point is 7.5 Mega Pascals (MPa). Challenges to using supercritical glycerin for extraction from plant materials include the need to prevent the supercritical glycerin from returning to its liquid state. However, temperatures higher than glycerin's boiling point may increase the decomposition of the desirable thermolabile bioactive compounds in the final extract.

There remains a need for improved high throughput methods of extracting bioactive compounds from plant materials.

SUMMARY OF THE INVENTION

The present invention provides efficient methods of extracting bioactive compounds from plant material using supercritical glycerin in combination with one or more inert co-solvents that lower the supercritical point of a mixture of glycerin and the inert co-solvent.

The invention provides a method for extracting selected bioactive compounds from plant materials by contacting bioactive compound-containing plant materials with a supercritical mixture of glycerin and one or more inert co-solvents in an amount effective to extract selected bioactive materials from the plant materials, wherein the one or more inert co-solvents lower the effective supercritical point of the supercritical mixture to its boiling point for a time effective to produce an extract containing the selected bioactive compounds.

An implementation of the method includes contacting the plant materials with a supercritical mixture of glycerin and one or more inert supercritical co-solvents at temperatures between approximately 550° K and approximately 700° K and at pressures between approximately 250 kPa and approximately 7500 kPa. In the method, the one or more inert co-solvents are selected from the group consisting of Helium, Neon, Argon, and Krypton, Carbon Dioxide, and Xenon gases. The plant materials may be obtained from cannabis plants and seeds and the bioactive compounds may be cannabinoids. Extracted bioactive compounds are obtained by the method of the invention.

BRIEF DESCRIPTION OF THE DRAWINGS

The advantages of the invention will become readily apparent to those skilled in the art from the detailed description of implementations of the invention when considered in the light of the accompanying drawings, in which:

FIG. 1 depicts an implementation of a supercritical fluid extraction apparatus for performing the methods of the invention.

DETAILED DESCRIPTION

The present invention provides a method of performing SFE of plant materials such as cannabis, containing bioactive compounds, using supercritical glycerin and a co-solvent, resulting in less viscous extracts in glycerin that are readily mixed and packaged by automation in line with the extraction process. The result is a high throughput extraction system.

In an implementation of the invention, a temperature above 554° Kelvin (290° C.) (the boiling point of glycerin) is used during extraction to prevent the supercritical glycerin from returning to a liquid state. However, temperatures higher than glycerin's boiling point may increase decomposition of desirable thermolabile bioactive products. Thus, in the method of the invention, the effective supercritical temperature point of the mixture of glycerin combined with one or more inert co-solvents is lowered to the boiling point of glycerin, limiting the decomposition rate to reasonable levels. The co-solvent used must be a non-reactive (inert) gas species with an effective supercritical point temperature below 310° Kelvin to provide optimal concentrations of glycerin in the extract, while reducing the supercritical point of the mixture. Suitable inert co-solvents include gases having low critical point temperatures and pressures and in particular gases that are non-reactive at 563° Kelvin that have a critical point temperature below 250° to 300° Kelvin. Suitable gases include Helium, Neon. Argon, and Krypton. Carbon dioxide and Xenon may be used as the co-solvent in higher amounts (based on the molar fraction of glycerin to co-solvent) however, the total glycerin content would constitute a lower percentage of the eluate, lessening efficiency by lowering the throughput of the apparatus used for the extraction.

In the method of the invention, a selected plant material is prepared, for example, by washing and/or fragmenting the material and is added to the main extraction chamber 10 before the extraction process begins. Referring to the system depicted in FIG. 1, at least one co-solvent gas such as helium, in an amount dependent on the selected extraction batch size, is added to a reservoir 12 and liquid glycerin is added to a separate reservoir 14. Multiple co-solvent gases may be used, in which case additional separate reservoirs may be added. At the initiation of the extraction process, the extractor 10 may be flushed with an inert gas, for example helium, and a mild vacuum is used to remove oxygen and other gaseous contaminates from the extractor 10.

When the system of FIG. 1 is placed in operation, the helium is released from reservoir 12 into a condenser 16 that condenses the helium to above its critical pressure at 227 kPa, forming supercritical helium. The condenser 16 releases the supercritical helium into a gas pump 18 that further raises the pressure to a pre-determined level for the mixture of supercritical glycerin and helium. In the case of the minimum viable temperature (563 Kelvin) for optimal conservation of glycerin, the pressure is at least or above 4975 kPa in a 35% Helium, 65% glycerin mixture. This ratio is determined using an Equation of State such as the Peng Robinson equation of state ("PR EOS," Peng, D. Y.; Robinson, D. B. (1976) *Industrial and Engineering Chemistry: Fundamentals* 15: 59-64.) The liquid glycerin is pumped from reservoir 14 via a liquid pump 20 to regulate the amount of glycerin introduced, dependent on the selected extraction batch size. The liquid pump 20 pumps the glycerin into a pre-heater 22 to raise the liquid glycerin to its vapor temperature so that the gases may be mixed. The vapor glycerin and the supercritical helium move through the individual back pressure regulators 24 and 26 into a proportioning valve 28, where they become a mixture. The proportioning valve 28 serves to ensure the correct preselected amounts of the two gases in the mixture is achieved; in this example, as a 35% Helium, 65% glycerin molar mixture. The proportioning valve 28 outputs to another heater 30, which ensures the two gases in the mixture are brought to the appropriate temperature of 563° K and remain above the 4975 kPa pressure. This supercritical mixture is then fed into the extractor 10 until that same pressure and temperature level is achieved and the supercritical mixture is allowed to mix with the plant material, extracting the compounds. The extractor 10 includes temperature and pressure sensors within its chamber to monitor and regulate the pressure and temperature. The supercritical mixture remains in the extractor 10 at the desired temperature and pressure for a period of time sufficient to extract the bioactive compounds from the specific plant material. The supercritical fluid mixture with the plant material is then expelled from the extractor 10.

After extraction is completed, the plant material is removed and the supercritical fluid product is cooled down to below 563° Kelvin to bring the glycerin containing the extracted bioactive products back to a liquid form, as the mixture passes through the separators 32, 34, 36 and 38, which recapture the helium to be used again, and remove the now liquid glycerin extract into a separate product container. At least one separator is used, however multiple separators may be used for a fractionation process to separate out specific bioactive compounds in multiple runs on the same batch of plant material using a fractionation column. The extract is then in a concentrated form of liquid glycerin with a viscosity lower than a pure oil, which can then be packaged or diluted further for use.

Different co-solvents may be used to obtain optimum amounts of desired bioactive products from a selected plant material. Co-solvents with higher supercritical temperatures will require a higher co-solvent to glycerin ratio. This means there will be less glycerin in the end, extracted product, and thus a higher ratio of extracted compounds to glycerin, i.e. a more concentrated solution. The lower the supercritical temperature of the co-solvent(s), the less concentrated the end product.

The present invention can be practiced other than as specifically illustrated and described herein without departing from its spirit or scope.

We claim:

1. A method for extracting selected bioactive compounds from plant materials comprising contacting selected bioactive compound-containing plant materials soluble in supercritical glycerin, with a supercritical mixture of glycerin and one or more non-reactive inert gas co-solvents with an effective supercritical point temperature below 301° Kelvin to provide optimal concentrations of glycerin in the extract while reducing the supercritical point of the mixture, at temperatures between approximately 550° K and approximately 700° K and at pressures between approximately 250 kPa and approximately 7500 kPa, in an amount effective to maintain the glycerin in supercritical phase for a sufficient time to extract the selected bioactive materials from the plant materials, wherein the one or more inert co-solvents lower the effective supercritical temperature of the supercritical mixture to its boiling point for a time effective to produce a glycerin extract containing the selected bioactive compounds.

2. The method of claim 1 wherein the one or more inert co-solvents are selected from the group consisting of Helium, Neon, Argon, and Krypton, Carbon Dioxide, and Xenon gases.

3. The method of claim 1 wherein the plant materials are obtained from cannabis plants and/or seeds.

4. The method of claim 3 wherein the bioactive compounds are cannabinoids.

\* \* \* \* \*